(12) United States Patent
Malota et al.

(10) Patent No.: US 11,626,211 B2
(45) Date of Patent: Apr. 11, 2023

(54) MODELLING BLOOD VESSELS AND BLOOD FLOW

(71) Applicant: KARDIOLYTICS INC., Tulsa, OK (US)

(72) Inventors: Zbigniew Malota, Tychy (PL); Wojciech Sadowski, Zabrze (PL)

(73) Assignee: KARDIOLYTICS INC., Tulsa, OK (US)

( * ) Notice: Subject to any disclaimer, the term of this patent is extended or adjusted under 35 U.S.C. 154(b) by 820 days.

(21) Appl. No.: 16/513,756

(22) Filed: Jul. 17, 2019

(65) Prior Publication Data

US 2020/0105420 A1    Apr. 2, 2020

(30) Foreign Application Priority Data

Sep. 28, 2018  (PL) .......................... 427234
May 16, 2019  (EP) ..................... 19174972

(51) Int. Cl.
| | |
|---|---|
| *G16H 50/50* | (2018.01) |
| *G16H 30/40* | (2018.01) |
| *A61B 5/026* | (2006.01) |
| *A61B 6/00* | (2006.01) |
| *G06T 7/60* | (2017.01) |
| *G06T 17/00* | (2006.01) |

(52) U.S. Cl.
CPC ............ *G16H 50/50* (2018.01); *G16H 30/40* (2018.01); *A61B 5/026* (2013.01); *A61B 6/504* (2013.01); *G06T 7/60* (2013.01); *G06T 17/00* (2013.01); *G06T 2200/04* (2013.01); *G06T 2207/30101* (2013.01)

(58) Field of Classification Search
None
See application file for complete search history.

(56) References Cited

U.S. PATENT DOCUMENTS

| 4,562,843 | A | * | 1/1986 | Djordjevich | G16H 40/63 600/490 |
|---|---|---|---|---|---|
| 2002/0002447 | A1 | * | 1/2002 | Keane | G06N 3/002 703/11 |
| 2014/0058715 | A1 | * | 2/2014 | Sharma | A61B 5/02 007 703/11 |

(Continued)

*Primary Examiner* — Sultana M Zalalee
(74) *Attorney, Agent, or Firm* — Mark M. Friedman (57) ABSTRACT

Method for modelling blood vessels includes: obtaining medical imaging data of the blood vessels; generating a three-dimensional personalized model of the blood vessels, based on the medical imaging data; generating a three-dimensional reference model of the blood vessels that reflects a state of healthy blood vessels that lack lesions, based on the medical imaging data or based on numerical reconstruction of the personalized model; performing a numerical simulation of blood flow for the same physical and boundary conditions in the personalized model and in the reference model, the simulation comprising determining conditions of blood flow at an inlet to the blood vessels model and calculating blood flow energy for the inlet and all outlets of the blood vessels model; comparing the blood flow energy measured for the personalized model and for the reference model; determining flow energy change indexes of the blood flow in the personalized model and the reference model.

14 Claims, 8 Drawing Sheets

(56) References Cited

U.S. PATENT DOCUMENTS

| | | | |
|---|---|---|---|
| 2014/0200867 A1* | 7/2014 | Lavi | G16H 50/30 |
| | | | 703/2 |
| 2014/0316758 A1* | 10/2014 | Yagi | A61B 17/12118 |
| | | | 703/9 |
| 2015/0065864 A1* | 3/2015 | Sharma | A61B 5/0263 |
| | | | 600/407 |
| 2015/0351703 A1* | 12/2015 | Phillips | A61B 8/5223 |
| | | | 600/301 |
| 2017/0068797 A1* | 3/2017 | Sharma | A61B 5/0263 |
| 2018/0344994 A1* | 12/2018 | Karavany | A61M 25/0023 |

* cited by examiner

MODELLING BLOOD VESSELS AND BLOOD FLOW

TECHNICAL FIELD

The invention relates to modelling blood vessels and blood flow in the modeled blood vessels. The invention is applicable as a tool for medical practitioners, and to assist in obtaining information about the cardiovascular state of a patient, which can be useful for further diagnosis of circulatory and cardiovascular diseases. One embodiment of the invention is a method, which as described herein, is independent of physiological characteristics of an individual patient.

BACKGROUND

Cardiovascular diseases are a serious problem, both in regard to its health and societal aspects. Atherosclerosis is a disease caused by lipoproteins, which leads to the formation of an atherosclerotic plaque at specific sites of an artery due to intramuscular inflammation, necrosis, fibrosis, and calcification. Stable forms of coronary heart disease can be often treated pharmacologically. In many cases, however, revascularization is necessary by means of either percutaneous angioplasty or through coronary artery bypass grafting (CABG), which redirects blood around a section of a blocked or partially blocked artery.

In order to determine the course of a disease and to select which therapeutic actions should be taken, it is necessary to conduct diagnostic tests. Currently, the basic methods for assessing the hemodynamic significance of coronary stenosis are cardiac stress tests, contrast angiography, and fractional flow reserve (FFR). Practically all methods for assessing the significance of hemodynamic coronary stenosis have some disadvantages.

The exercise stress test allows assessment of the heart's function in response to increased physical effort and increased oxygen demand. It is a stress test and therefore, there are numerous contraindications to its performance, such as: very advanced ischemic heart disease, advanced aortic valve disease, severe heart failure, acute infection, recent stroke, unstabilized arterial hypertension and osteoarthritis.

In turn, contrast angiography, despite being a high spatial resolution test, has limitations related to image analysis and the invasive nature of the procedure. One of the limitations is the fact that visualization of the cross-sectional area of the vessel does not provide any information about the arterial wall. Another limitation is that the three-dimensional image demonstrating the course of arteries, mapped on two-dimensional plane, causes that on various images eccentric atherosclerotic plaques are projected as changes having variable degree of stenosis.

Fractional flow reserve measurement is also an invasive technique, performed during angiography, to measure pressure differences across a region of coronary artery stenosis. However, a non-linear relationship between pressure-flow, as well as the influence of external vessel forces, size of the perfusion area, microvascular dysfunction, as well as catheter-induced errors in invasive measurements of pressure can affect the accuracy of FFR assessment. The use of FFR requires a deep knowledge of the anatomy, physiology, and pathophysiology of coronary arteries. The degree of narrowing does not transfer easily into the functional significance of the change. The decision about revascularization in relation to intermediate stenosis, when reduction in the diameter of the artery lumen is in the range from 50% to 70%, is particularly controversial. It is estimated that about half of them are hemodynamically significant, although they are often overlooked at revascularization.

Inconveniences and risks for patients associated with these tests are widely known and led to the development of supportive methods of obtaining information about the cardiovascular system, the results of which are intended for medical practitioners and can be used to assess changes occurring in cardiovascular diseases.

SUMMARY OF THE INVENTION

The purpose of certain embodiments of this invention is to solve problems that occur in known methods of supplementing information on cardiovascular diseases, the results of which are intended for medical practitioners and which can be used in further diagnostics. Essentially, the analysis of blood flow dynamics in generated models reflecting blood vessels itself is very difficult mainly due to complex geometry of the blood vessels, the flexibility of their walls, non-Newtonian properties of blood, pulsatile flow and variable vascular resistance, during the diastolic and systolic phases of the cardiac cycle. Particular difficulties are related to both the lack of detailed clinical data as well as individual (personalized) differences in cardiovascular physiology enabling precise mathematical and physical models generation.

The invention relates to a method for modelling blood vessels, the method in one embodiment comprising: obtaining medical imaging data of the blood vessels; generating a three-dimensional personalized model of the blood vessels, based on the medical imaging data; generating a three-dimensional reference model of the blood vessels that reflects a state of healthy blood vessels that lack lesions, based on the medical imaging data or based on numerical reconstruction of the personalized model; performing a numerical simulation of blood flow for the same physical and boundary conditions in the personalized model and in the reference model, the simulation comprising determining conditions of blood flow at an inlet to the personalized model and calculating blood flow energy for the inlet and all outlets of the personalized model and determining conditions of blood flow at an inlet to the reference model and calculating blood flow energy for the inlet and all outlets of the reference model; comparing the blood flow energy measured for the personalized model and for the reference model; and determining flow energy change indexes of the blood flow in the personalized model and in the reference model.

The method may comprise generating the reference model based on the personalized model, by eliminating stenoses existing in the personalized model, resulting from atherosclerosis lesions, by numerical modification of the blood vessel geometry in areas of said stenoses to obtain a hypothetically healthy of blood vessel model, as the reference model prior to the onset of the lesions.

The method may comprise generating the reference model based on the personalized model, by eliminating one stenosis, in one branch only, without reconstruction changes in geometry in other branches.

The method may comprise conducting the blood flow simulation for both personalized and reconstructed models, for an increasing inlet blood flow rate, from laminar flow until achieving a developed turbulent flow.

The method may comprise applying a variable blood flow rate on the inlet of both personalized and reconstructed models.

The method may comprise conducting the blood flow simulation in personalized model for inlet and outlet boundary conditions obtained from the simulation results of reference model.

The method may comprise simulating a linear increase of blood flow rate on the inlet to the blood vessels model (for whichever blood vessels model is being used, personalized or reference).

The method may comprise simulating a pulsatory change of blood flow rate, having a variable amplitude or a variable frequency, on the inlet to the blood vessels model (for whichever model is being used, personalized or reference).

The method may further comprise further comprising determining an absolute flow energy change index (ΔEf), as a difference between the flow energy in the branch of the personalized model and the flow energy in the same branch of the reference model.

The method may further comprise determining a relative flow energy change index (EFR), as a relationship of the flow energy in any selected, one or more, branches of the models both personalized and reference, in relation to the inlet energy of flow.

The method may comprise determining the flow energy change indicators over a wide range of flow rates including under conditions of maximal vasodilation as well as outside of physiological conditions.

The method may comprise determining the flow energy change indexes on a basis of linear or polynomial approximations of a function of the flow energy change with respect to the flow rate (EFR).

The method may comprise determining the indexes of flow energy change during the diastolic phase in wave free period, when the hemodynamic conditions are substantially independent on the pulse rate, as well when the resistance is minimal, substantially constant and a pressure gradient is proportional to the flow rate.

The method may comprise determining other, absolute and relative indexes of hemodynamic parameters, including at least one of: vascular resistance, pressure drop, turbulence kinetic energy (TKE), wall shear stress (WSS), oscillatory shear (OSI) and residence time (RRT), which are a function of pressure (stress) and flow rate of the personalized model compared to the reference model.

The invention also relates to a computer-implemented system (200) for modelling blood vessels, the system comprising: an input for obtaining medical imaging data of the blood vessels; a personalized model generator (202) configured to generate a three-dimensional personalized model of the blood vessels, based on the medical imaging data; a reference model generator (203) configured to generate a three-dimensional reference model of the blood vessels that reflects a state of healthy blood vessels that lack lesions, based on the medical imaging data or based on numerical reconstruction of the personalized model; a blood flow numerical simulator (205) configured to perform a numerical simulation of blood flow for the same physical and boundary conditions in the personalized model and in the reference model, the simulation comprising determining conditions of blood flow at an inlet to the personalized model and calculating blood flow energy for the inlet and all outlets of the personalized model and determining conditions of blood flow at an inlet to the reference model and calculating blood flow energy for the inlet and all outlets of the reference model; and a comparative analysis module (207) configured to compare the blood flow energy measured for the personalized model and for the reference model and to determine flow energy change indexes of the blood flow in the personalized model and in the reference model.

An advantage of the invention is that it allows for modelling of blood vessels and blood flow in these blood vessel models (i.e. personalized models and reference models) based only on non-invasive medical imaging data, such as computed tomography.

The analysis of blood flow in the generated models of blood vessels is carried out independently of the physiological properties of a particular patient.

The use of the comparative method, where relative indexes are determined based on a comparison of two models, stenosed and reconstructed, of the same patient makes it possible to significantly limit the influence of errors on the final result of the test.

Possible errors occurring during generation of blood vessel models are basically reproduced in both compared models: the personalized model and the reference model—so the impact of these errors on the calculated indicators of the flow energy is minimal.

In contrast to other non-invasive tests developed for the assessment of hemodynamic significance of coronary stenosis, this test does not require additional clinical trials, the measure of flow distribution, pressure or peripheral vascular resistance, and does not require determining additional conditions of maximal hyperaemic flow during vasodilation. The incorrect description of microcirculatory vasodilation may lead to an incorrect assessment of the FFR and hemodynamic significance of coronary stenosis.

The method allows simulating blood flow, in models of blood vessels, under the same physical and boundary conditions, when the blood flow conditions at the inlet and/or outlet to the blood vessel models are regulated, and the flow energy is measured in all branches of these models.

Blood flow in the blood vessels can be increased to values greater from typical physiological values that cannot be achieved in typical clinical tests.

The comparing flow in two models with predetermined initial and boundary conditions allows for evaluation of the results not only independently of physiological and pathophysiological conditions, but also allows flow modelling without accurate knowledge of the distribution of flow, pressure or peripheral vascular resistance, suitable for each patient.

When simulating blood flow in blood vessel models, and especially coronary vessels, very often physiological parameters, such as blood viscosity, intra-arterial pressure and left ventricular pressure, can be set to a known average of population-specific values, and not values that require detailed clinical trials of the patient.

The method allows the medical practitioner that analyzes the results of the blood flow simulation in the blood vessel models, to obtain additional diagnostic information that may be useful to assess the nature and significance of changes occurring in the examined cardiovascular model without the necessity for additional tests of the patient. In particular, this is possible by providing the medical practitioner with the flow energy change index. The linear dependence between this energy index and flow rate, at a certain flow rate range or at a particular phase of the cardiac cycle, allows a very accurate determination of the value at which the lesion, such as a plaque causing vascular stenosis, is significant for the entire cardiovascular system. In certain embodiments, the use of the method of the invention also has a positive economic impact, by making it possible to limit the number of invasive tests at the initial stages, and as a tool to support the work of medical practitioners it will allow reduction of the costs associated with invasive tests and procedures of patients with cardiovascular diseases. The reduction in the number of invasive tests and treatments results not only in the reduction of costs, but also in the reduction of patient risks, and complications associated with the implementation of invasive procedures, and thus, improving the results of long-term treatment of patients.

BRIEF DESCRIPTION OF THE DRAWINGS

The invention is presented herein by means of non-limiting example embodiments shown in a drawing, wherein.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention.

The method of modelling blood vessels and blood flow in these blood vessel models allows one to determine various information on blood flow, using for this purpose only non-invasively collected patient information. The modelling method may refer to blood flow in any blood vessels, such as coronary, cervical, peripheral vessels, abdominal cavities, kidneys and cerebral vessels.

Figure 1A:
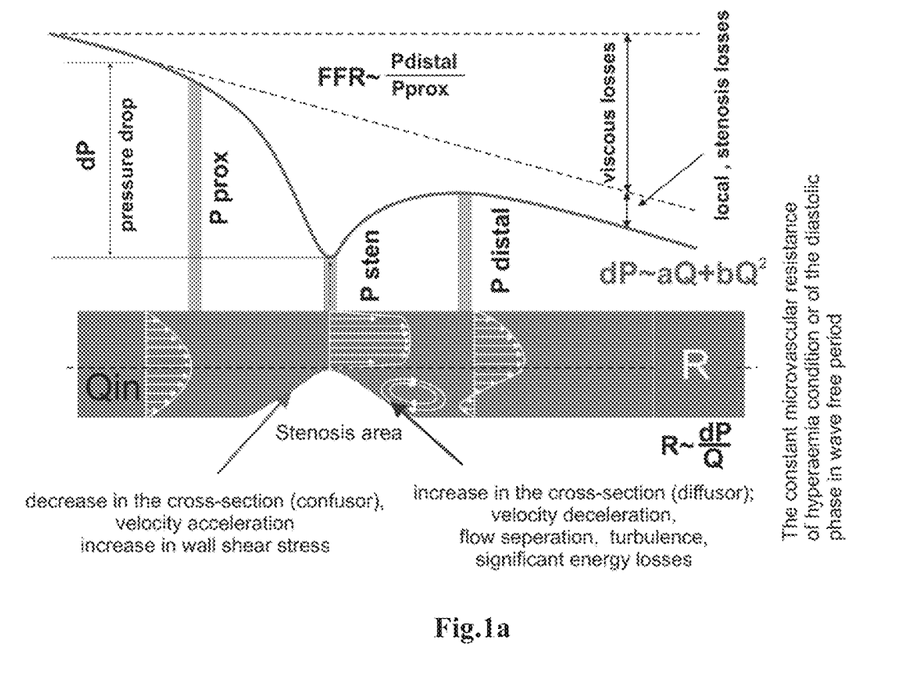
FIG. 1a shows the flow through a stenotic vessel division of the stenosis area into converging, narrowing, and a diverging section.

The flow through a stenotic vessel can be divided on the area into converging, narrowing, and a diverging section, each with their particular pressure-flow relations (FIG. 1a).

The pressure drop along the length of a narrowed vessel, friction (viscous) losses are linearly related to the flow through the stenosis, whereas exit losses increase with the square of flow, resulting in a non-linear relation between pressure gradient and flow velocity.

The function is a quadratic polynomial where the first element determines the effect of the viscosity forces and the second one is due to convective acceleration, which leads to flow separations and energy losses due to turbulence flow. In the case of pulsatile flow, there is also a third segment that is related to the activity of the inertial forces.

A very big challenge posed by coronary flow modelling is the fact that the coronary circulation possesses a high degree of pressure-flow autoregulation and metabolic adaptation which together maintain stable coronary flow at a level that meets myocardial demand.

Furthermore, the mechanisms underlying autoregulation are not entirely understood. It is well recognized that coronary blood flow and overall myocardial oxygen delivery is closely coupled to myocardial oxidative metabolism.

Due to the regulation of coronary vascular resistance (vasodilation), blood flow is maintained relatively constant over a wide range of perfusion pressures (~60-120 mmHg), which depends on a variety of physiologic as well as pathologic stimuli such as perfusion pressure, metabolism, hypoxemia, and myocardial ischemic.

Outside this range, flow becomes pressure-dependent and the loss of autoregulation is observed.

Autoregulation also does not occur when the system is maximally constricted as well as maximally dilated (maximal vasodilation), e.g. following the administration of vasodilator agents.

The invention presents two modelling methods of blood vessels and blood flow, both based on the flow energy loss compare analysis between personalised and references models.

The first modelling method is carried out outside of the autoregulation range, while the second one includes autoregulation.

Figure 1B:
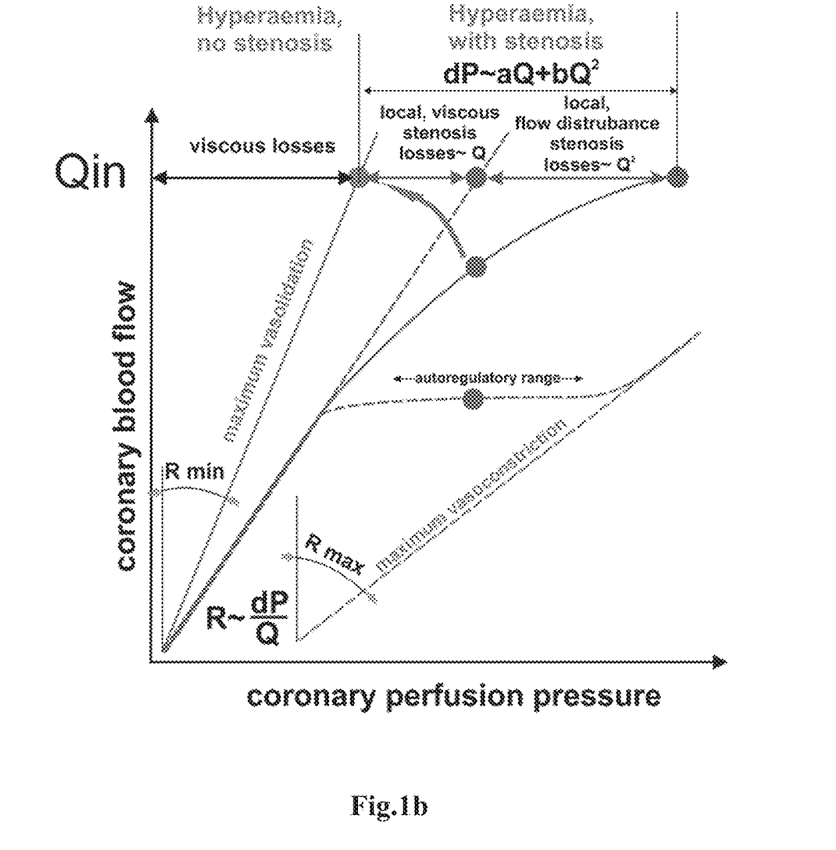
FIG. 1b shows Coronary perfusion pressure-flow relationship in the presence of stenosis.

During modelling of blood vessels, the inlet flow may vary both in terms of linearity as well as its pulsatile nature. Under ideal laminar constant flow conditions, in which vascular resistance is independent of flow and pressure, without taking into account autoregulation in numerical simulation, for the vessel without stenosis, the increase in the flow rate causes a linear increase in the pressure gradient (FIG. 1b). The vessel resistance is constant. However, the flow disturbance induced by stenosis or vessel shapes causes a deviation from this law. The appearance of vessel narrowing causes an additional pressure drop and the pressure gradient flow-rate relationship can be described by means of a quadratic polynomial.

In the case of pulsated flow during the diastolic phase in the wave free period, when the hemodynamic conditions are substantially constant and independent of the pulse rate, the pressure gradient is linearly proportional to the flow rate and the resistance is minimal and constant.

For this reason, in this invention, the analysis of blood flow has been used in a very wide flow rate range.

In particular, it applies to laminar flow, transitional flow, developed turbulent flow, flow in conditions of maximal vasodilation as well as flow during the wave free period of pulsatile flow.

For the first modelling method (FIG. 2a), we assume that microvascular resistance is constant.

Figure 2A:
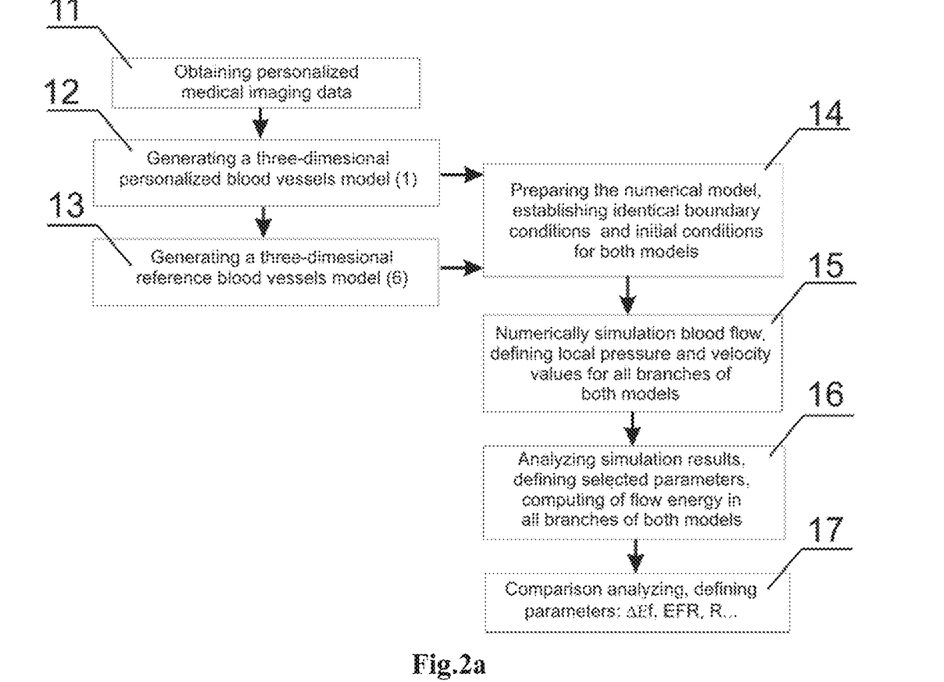
FIG. 2a shows, in a simplified block diagram, the first method of modelling blood vessels and blood flow in these blood vessels models, in accordance with an embodiment of the invention.
Figure 3:
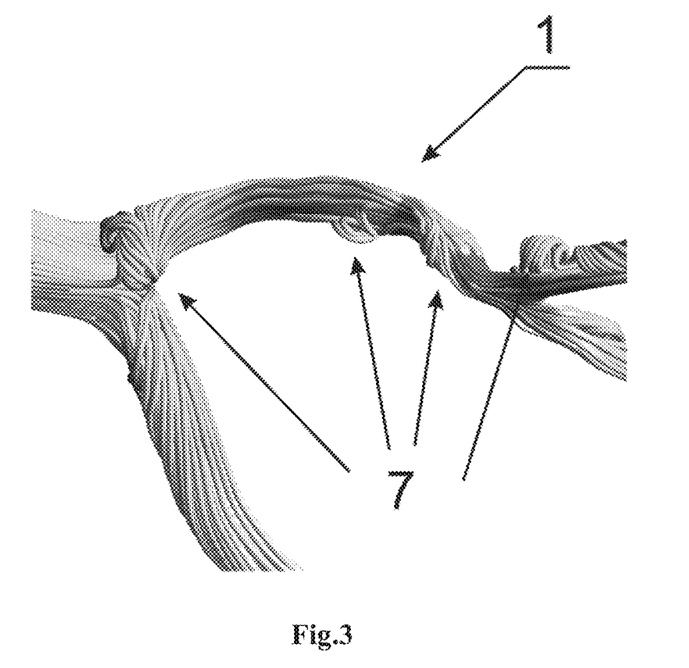
FIG. 3 shows a personalized blood vessels model with visible velocity streamlines and marked flow disturbances, in accordance with an embodiment of the invention.
Figure 6:
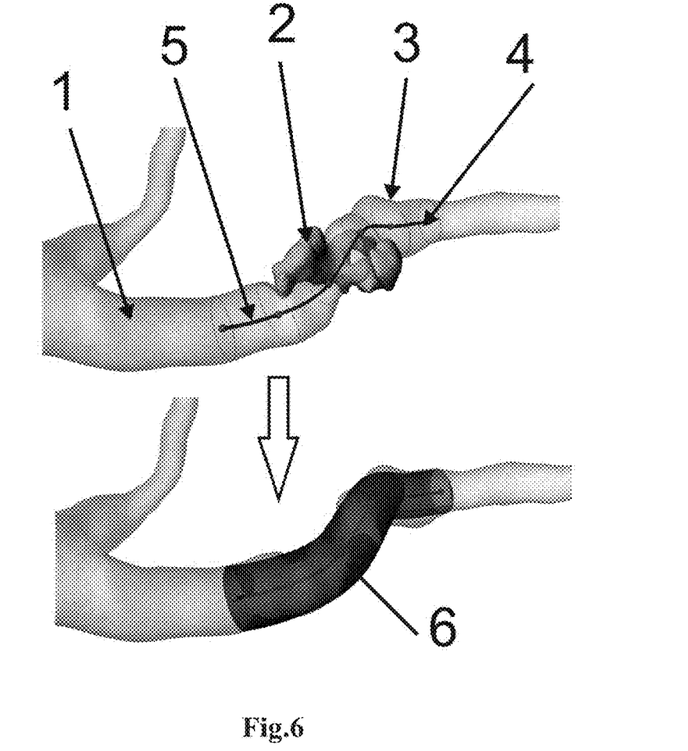
FIG. 6 shows a schematic view of a personalized model with atherosclerosis plaques as well the reference model after numerical reconstruction of the blood vessel at the site of the stenosis, in accordance with an embodiment of the invention.

In the method as shown in FIG. 2a, a personalized three-dimensional model 1 of blood vessels (as shown in FIG. 3) is generated in step 12, in this particular case the patient's coronary vessels model. The personalized model 1 is generated based on the segmentation 3, 4 (as shown in FIG. 6) of the medical imaging data obtained in step 11. For this purpose, available computer tomography scan data stored in a data storage are used. Alternatively, magnetic resonance imaging or angiography data could be used for this purpose. The coronary vessel system comprises a complex vessel network, from large arteries to arterioles, capillaries, and veins. The exemplary personalized blood vessels model 1, includes the Left Main Coronary Artery LMCA, the Left Anterior Descending Artery LAD with distal branches LAD1, LAD2, the left circumferential artery CX together with the marginal branch CX2.

Figure 4:
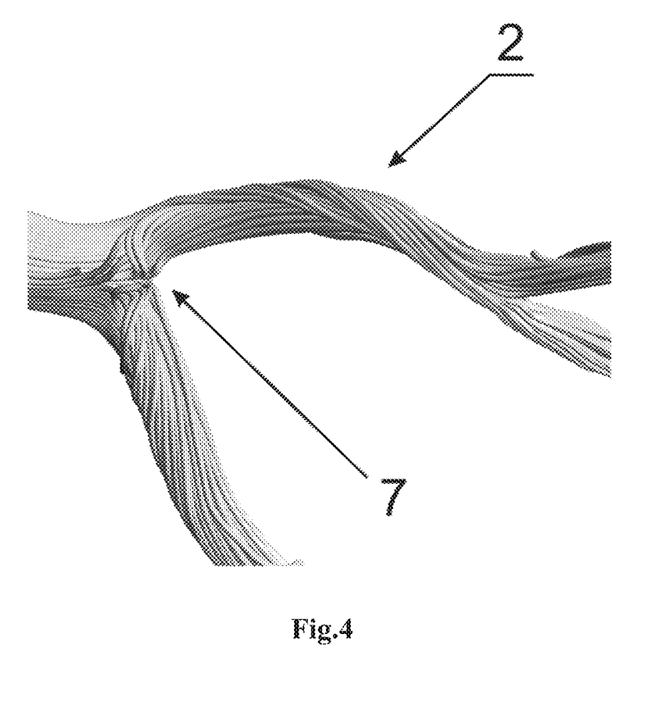
FIG. 4 shows a reference blood vessels model with visible velocity streamlines and marked flow disturbances, in accordance with an embodiment of the invention.
Figure 5:
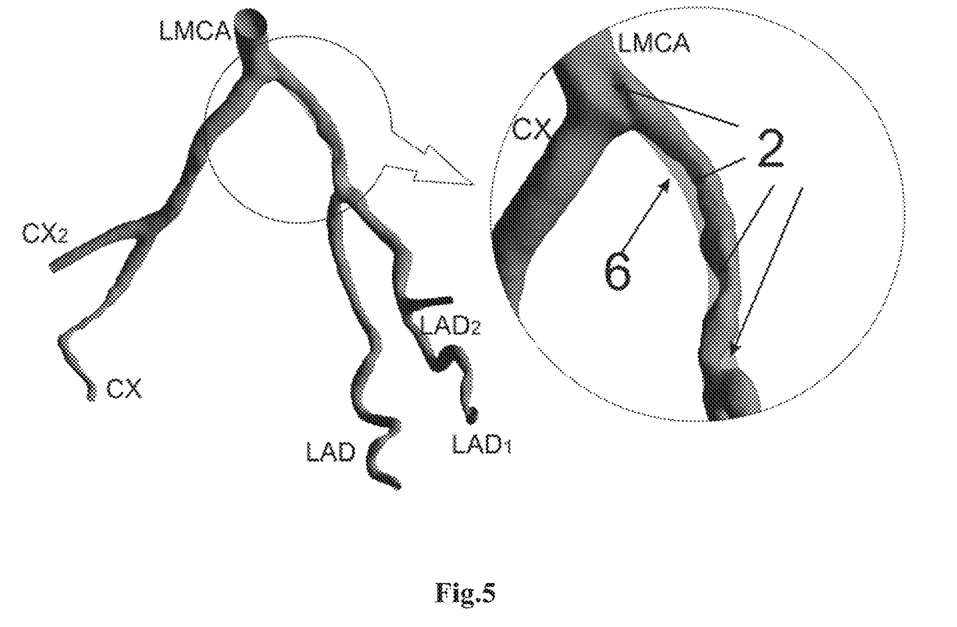
FIG. 5 shows a comparison of a three-dimensional personalized blood vessels model with a reference model, in accordance with an embodiment of the invention.

Subsequently, a reference three-dimensional model 6 of the blood vessels (as shown in FIG. 4), that reflects the condition of healthy blood vessels and lacks lesions 2 visible in the medical imaging data (such as data of computer tomography imaging with contrast), is generated in step 13 on the basis of the medical imaging data or on the basis of personalized blood vessels model 1. To prepare the reference model 6, the existing lesions 2 in the form of stenoses that induced disturbance of flow 7, are removed from the personalized blood vessels model 1 by numerically modifying the geometry of the blood vessel at the sites of these stenoses in order to obtain a model of a hypothetically healthy blood vessel prior to the onset of lesions. The numerical modification of the geometry of the blood vessel is made on the basis of the approximation of the cross-sectional area in front of and behind the stenoses and curvature of the center line 5 of the vessel. The numerical modification of the geometry of the blood vessels itself may be performed in any three-dimensional graphics software known in the art.

After the personalized model 1 and the reference model 6 are generated, in both these models 1 and 6, using the finite element method (FEM) a volumetric calculation grid is generated in step 14, for which the equation of blood flow dynamics is solved in each node to determine local velocity and pressure values, which are used at a later step of comparing the generated models 1, 6 between each other.

Figure 7:
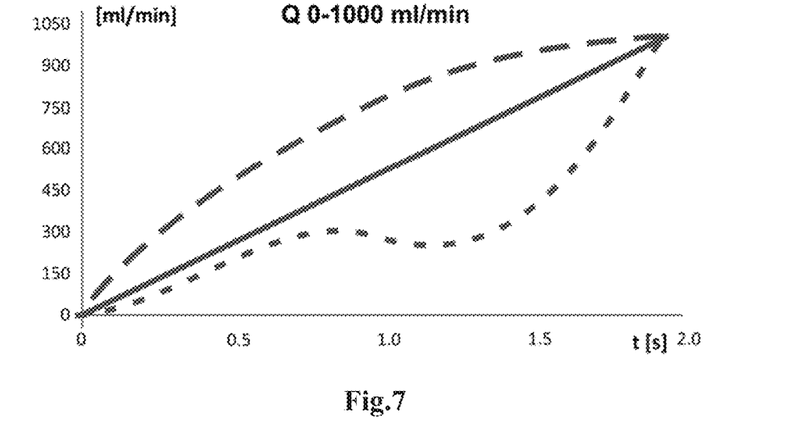
FIG. 7 shows a graph demonstrating a flow rate versus time curve, applied at the inlet to the blood vessels model, in accordance with an embodiment of the invention.

In the next step 15, numerical simulation of blood flow is performed for pre-established identical physical and boundary conditions in both generated models 1, 6, wherein during the flow simulation, the blood flow conditions are established and regulated on the inlet to the models, and simultaneously on the inlet and on every outlet of these models the energy of blood flow is calculated. Depending on necessity, the blood flow conditions on the inlet to the model may vary significantly between individual tests. The numerical flow simulation is carried out for an increasing inlet flow rate, essentially from the absence of flow, through the start of the flow, i.e. the laminar flow without disturbances, until achieving a developed turbulent flow. In the case of the modelled coronary vessel system of the patient, the maximum flow rate can be set at 15 ml/s, wherein the flow rate can be increased linearly (FIG. 7) over a time of 2 seconds until the value of 15 ml/s is reached. Conducting such simulation during the transition from laminar to turbulent flow, it is possible to spot an additional change in energy between the examined blood vessels models 1, 6, which is associated with turbulence and flow separation.

Figure 8:
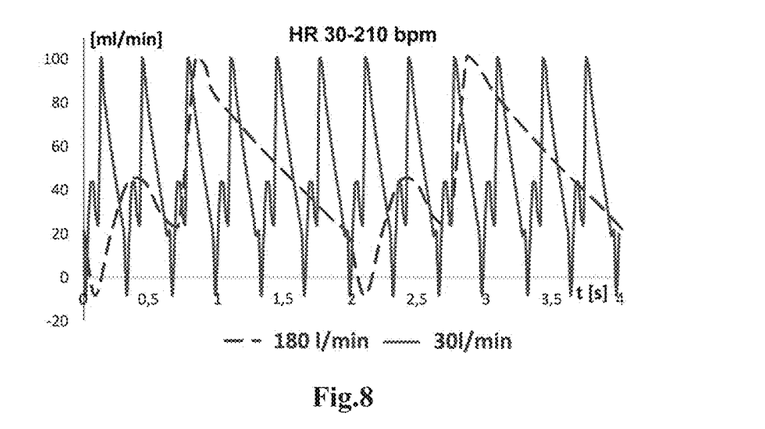
FIG. 8 shows a graph of blood flow rate pulsation versus time, with different pulse frequency, set at the inlet to the vasculature, in accordance with an embodiment of the invention.

The blood flow modelling can also be performed under pulsatile flow conditions (FIG. 8) by varying the flow rate over time according to a typical flow rate curve appropriate for the modelled coronary vessel system. Additionally, changes in pulse of amplitude or frequency in blood flow rate on the inlet to the vasculature may be simulated.

Figure 10:
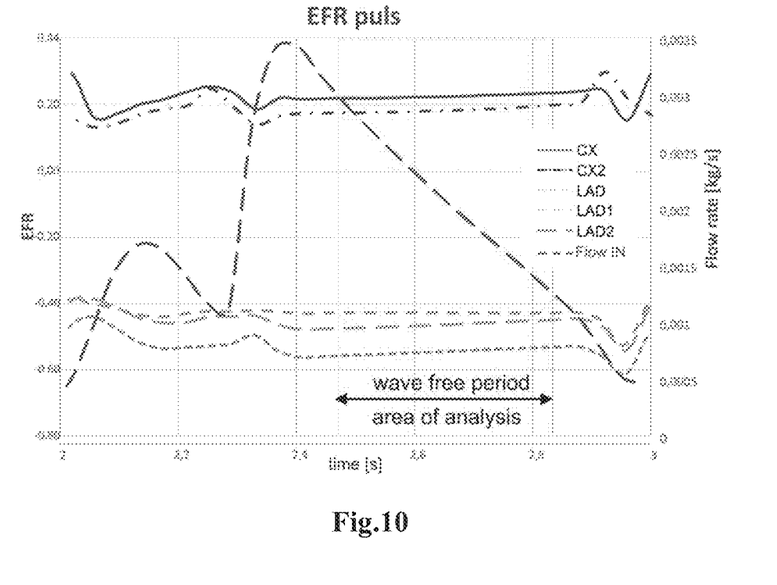
FIG. 10 shows a graph demonstrating the scope of the analysis area (wave free period) of the flow energy coefficient for the test with the given inlet pulsatile mass flow rate characteristic for the left coronary vessel, in accordance with an embodiment of the invention.

In particular, the analysis of blood flow in the period during the diastolic phase, in wave free period, allows the determination of changes in the flow energy, when the hemodynamic conditions are substantially independent of the pulse rate, as well and when the resistance is minimal, substantially constant and a pressure gradient is proportional to the flow rate (FIG. 10).

Predetermined physical and boundary conditions for which blood flow in blood vessels is simulated in step 15 and for which flow energy is calculated in step 16 allow easy comparison of the obtained results between the personalized model 1 and the reference model 6 in step 17.

It allows one to determine the absolute flow energy change index $\Delta Ef$, as the difference between the flow energy in the branch of the personalized model 1 and the flow energy in the same branch of the reference model 6.

The energy of the flow stream through the blood vessels system can be estimated as the product of the total pressure, i.e. the sum of the dynamic and static pressure and the flow rate through the surface perpendicular to the axis of the vessel. The stream energy, expressed in Watts, can be presented as:

$$Ef = \left(\frac{1}{2}U^2 + \frac{P}{\rho}\right)Q$$

According to the law of conservation of energy, total losses of energy during flow through the system of blood vessels may be estimated as an energy difference between the inlet to the vessel and the outlet from all branches of the vessels:

$$\dot{E}_{loss} = -\sum\left(p + \frac{1}{2}\rho u_i u_i\right)u_i S_i$$
$$= \sum (P_{total})Q_{in} - \sum (P_{total})Q_{out} = \sum Ef_{in} - \sum Ef_{out}$$

wherein: $\rho$ is the blood density, p is the static pressure of blood, $u_i$ are components of the velocity vector perpendicular to the surface of flow Si.

The absolute flow energy change index $\Delta Ef$, which expresses the changes of flow energy in individual branches of the personalized model 1 with respect to the flow energy in individual branches of the reference model 6 can be presented as:

$$\Delta Ef = Ef_{sten} - Ef_0$$

wherein:

$Ef_{sten}$ is the flow energy in the branch of the personalized model, and $Ef_0$ is the flow energy in the same branch of the reference model.

In those branches where there is stenosis, the absolute flow energy change index ΔEf has negative values. The lower the ΔEf value, the greater is the impact of lesions on blood flow. If there is any stenosis in the modelled blood vessels system, then in the branches of this system in which there is no stenosis the ΔEf value is positive.

It is convenient to show the ΔEf is relative to the flow energy in branches of the reference models 6. In this case, when the stenosis induces a drop in the flow energy, energy flow relative index (EFR) can be presented as:

$$EFR1 = \frac{\Delta Ef}{Ef_0} = \frac{Ef_{sten} - Ef_0}{Ef_0} = \frac{Ef_{sten}}{Ef_0} - 1$$

EFR takes negative values, less than 0 and greater than −1. The more the value of this parameter is closer to −1, the greater is the hemodynamic significance of stenosis in a given branch of coronary.

The existence of stenosis in any branch, especially outside the scope of autoregulation, in order to maintain system efficiency and the same blood flow rate, as compared to the reference model, requires more energy to flow. For this reason, the EFR can also be expressed relative to the inlet energy flow as the flow energy dependency in any branch of the personalized model 1 and inlet flow energy in the reference model 6 from the flow energy in the same branch of the reference model 6 and inlet flow energy in the personalized model 1.

In order to analyze and compare the energy losses, it is convenient to present the EFR parameter in the same range [0,1]. For this purpose a min-max normalization, i.e. scaling of values of the parameter EFR by dividing it by the maximal value, may be conducted.

The flow energy flow index EFR is a parameter that allows one to determine the hemodynamic effect of stenosis or other pathological change in the blood vessels system separately in all of its branches. In the case of high blood flow rates, the dependence of the relative flow energy change index EFR on the blood flow rate (Reynolds number), is linear with a very small curve slope, therefore this parameter allows to determine accurately relative flow energy change index EFR, which will allow the medical practitioner allows to determine of the hemodynamic significance of the stenosis.

The second method of modelling blood vessels and blood flow (FIG. 2b), in contrast to the first method (FIG. 2a), is based on the assumption of a constant flow rate in individual branches regardless of the existence of stenosis and its degree.

Figure 2B:
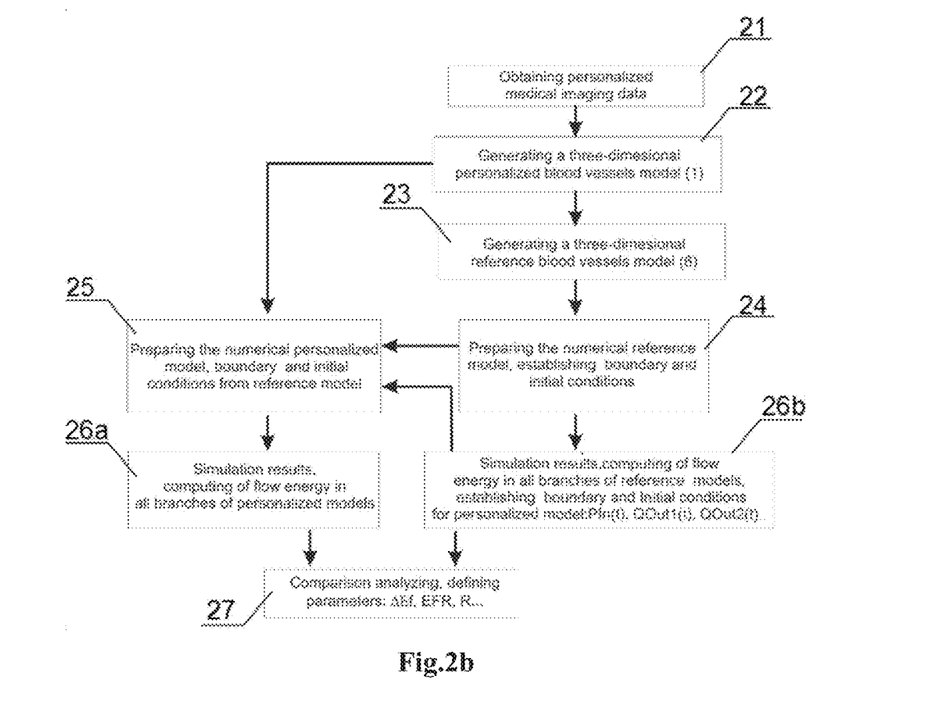
FIG. 2b shows, in a simplified block diagram, the second method of modelling blood vessels and blood flow in these blood vessels models, in accordance with an embodiment of the invention.

In this method, in steps 21, 23, 24, 26b the flow simulations in reference (reconstructed) model are carried out, with boundary and initial conditions the same as in the first method.

However, in the steps 22, 25, 26a of this method, when the flow simulation in a personalized model is performed, the initial boundary conditions at the outlets branches are based on the results obtained from the step 24 of blood flow modelling in the reference (reconstructed) model. The flow rate at the outlets in all branches of the personalized model is the same as the flow rate in the reconstructed model obtained from the simulation. In this way, this modelling method is independent of the degree of stenosis, similarly to maintaining constant flow rate, independent of perfusion pressure, during autoregulation of blood flow.

The maintaining constant flow rate in the branch of a personalized model with a stenosis requires more energy flow compared to flow in the same branch without being narrowed in the reference model. Therefore, the relative energy loss factors, can be calculated having regard to the difference between inlet and outlet energy, as:

$$EFR2 = \frac{(Ef_{sten\_in} - Ef_{sten}) - (Ef_{0\_in} - Ef_0)}{(Ef_{0\_in} - Ef_0)} = \frac{(Ef_{sten\_in} - Ef_{sten})}{(Ef_{0\_in} - Ef_0)} - 1$$

wherein:
$Ef_{sten\text{-}in}$ is the inlet flow energy in the personalized model;
$Ef_{0\text{-}in}$ is the inlet flow energy in the reference model.

It is also recommended to reconstruct the stenosis in one branch only, without reconstruction changes in geometry in other branches. This will enable a completely independent energy loses analysis only in the selected branch.

Based on the comparison, in step 27, of the flow energy losses of the personalized model and a reference model, also other hemodynamic parameters, which depended on the size of flow disturbances caused by vessel stenosis, can be specified by functions of pressure (stress) and of flow rate.

Among them, we can distinguish absolute and relative indexes of: vascular resistance R, turbulent kinetic energy, TKE pressure drop DP, wall shear stress WSS, shear oscillators OSI or residence time RRT.

Changes of cross-section of the blood vessel cause changes of vascular resistance of blood flow. A relatively small reduction of the diameter of the blood vessel has an explicit influence on the flow resistance, because the flow, according to the Hagen-Poiseuille law, is related to the $4^{th}$ power of the diameter of clearance of the vessel.

For example, a vascular resistance R may also be used in obtaining additional information on the modelled coronary vessel system. The results of vascular resistance calculations can be very helpful in further diagnostics. Changes in the cross-section of the blood vessel cause changes in the resistance of vascular blood flow. The relatively small reduction of the diameter of the blood vessel has explicit effect on the flow resistance in the modelled blood vessels, because the flow according to the Hagen-Poiseuille law, is associated with the fourth power of the vessel clearance diameter.

The resistance of particular branches of coronary vessels in the personalized model and the reference model can be calculated using the following formula:

$$R = \frac{\Delta P}{Q} = \frac{P_{in} - P_{out}}{Q_{out}}$$

wherein:
$P_{in}$ is the pressure on the inlet to the modelled blood vessels system;
$P_{out}$ is the pressure on the outlet of the selected branch of the modelled blood vessels system;
$Q_{out}$ is the flow rate in this selected branch of the modelled blood vessel system. The flow disorders are closely related to turbulent kinetic energy (TKE). For turbulent flow, the velocity can be represented as the sum of the mean value and fluctuation component and the kinetic energy of turbulence can be specified as the root mean square velocity fluctuations:

$$TKE = \tfrac{1}{2}\rho \overline{u'_j u'_j} = \tfrac{1}{2}\rho(\overline{u'^2_1} + \overline{u'^2_2} + \overline{u'^2_3})[mJ\ kg^{-1}]$$

where $u'_j$ is the fluctuation of the j-th velocity component.

The wall shear stress (WSS) is the tangential frictional force on the endothelial surface. For a Newtonian fluid flow in the straight vessel the shear stress is proportional to the flow shear and can be expressed as:

$$WSS = \mu \frac{\partial u}{\partial n}\Big|_{wall}$$

where m is the dynamic viscosity, u is the flow velocity parallel to the wall.

Additionally, in the case of pulsating flow the oscillatory shear index OSI and residence time RRT indexes, based on the temporal fluctuation of the WSS, may be computed respectively as follows:

$$OSI = \frac{1}{2}\left(1 - \frac{\left|\int_0^T \overline{WSS}\,dt\right|}{\int_0^T |\overline{WSS}|\,dt}\right)$$

$$RRT = \left[(1-2OSI)\frac{1}{T}\int_0^T |\overline{WSS}|\,dt\right]^{-1}$$

The blood flow energy itself can be specified in any computer program for numerical liquid flow simulation. Knowing the distribution of the flow energy in individual branches of the personalized model 1 and the distribution of energy in the branches of the reference model 6, it is possible to assess the amount of energy loss, in this example for coronary artery, caused by the stenosis.

Figure 9:
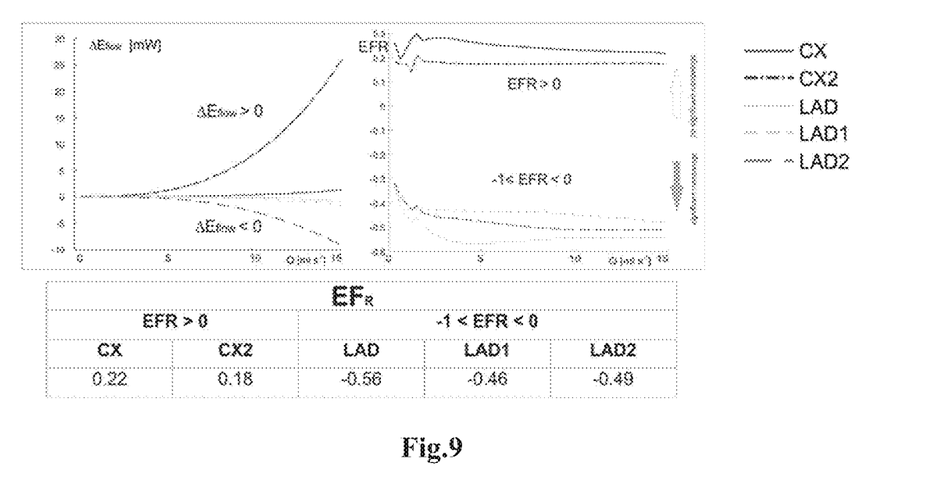
FIG. 9 shows a graph of an absolute flow energy index and a relative flow energy index versus flow rate as well specified normalized index of energy losses (EFRn) indexes in all branches of coronary models, in accordance with an embodiment of the invention.

For the modelled coronary vessel system, both the absolute flow energy index ΔEf and the relative flow energy index EFR is calculated. The results are presented in the form of diagrams and a table (FIG. 9, FIG. 10) and prepared for further analysis.

Based on the comparison of the obtained blood flow energy results between the personalized model 1 and the reference model 6, it is possible to determine other relative, to both models, hemodynamic parameters that are a function of pressure or stress.

The obtained results of blood flow modelling in the blood vessels models are basically intended for medical practitioners and may be helpful in further stages of diagnostics. The blood vessels modelling itself and flow modelling in these blood vessels models are carried out independently from the physiological conditions of a particular patient.

Figure 11:
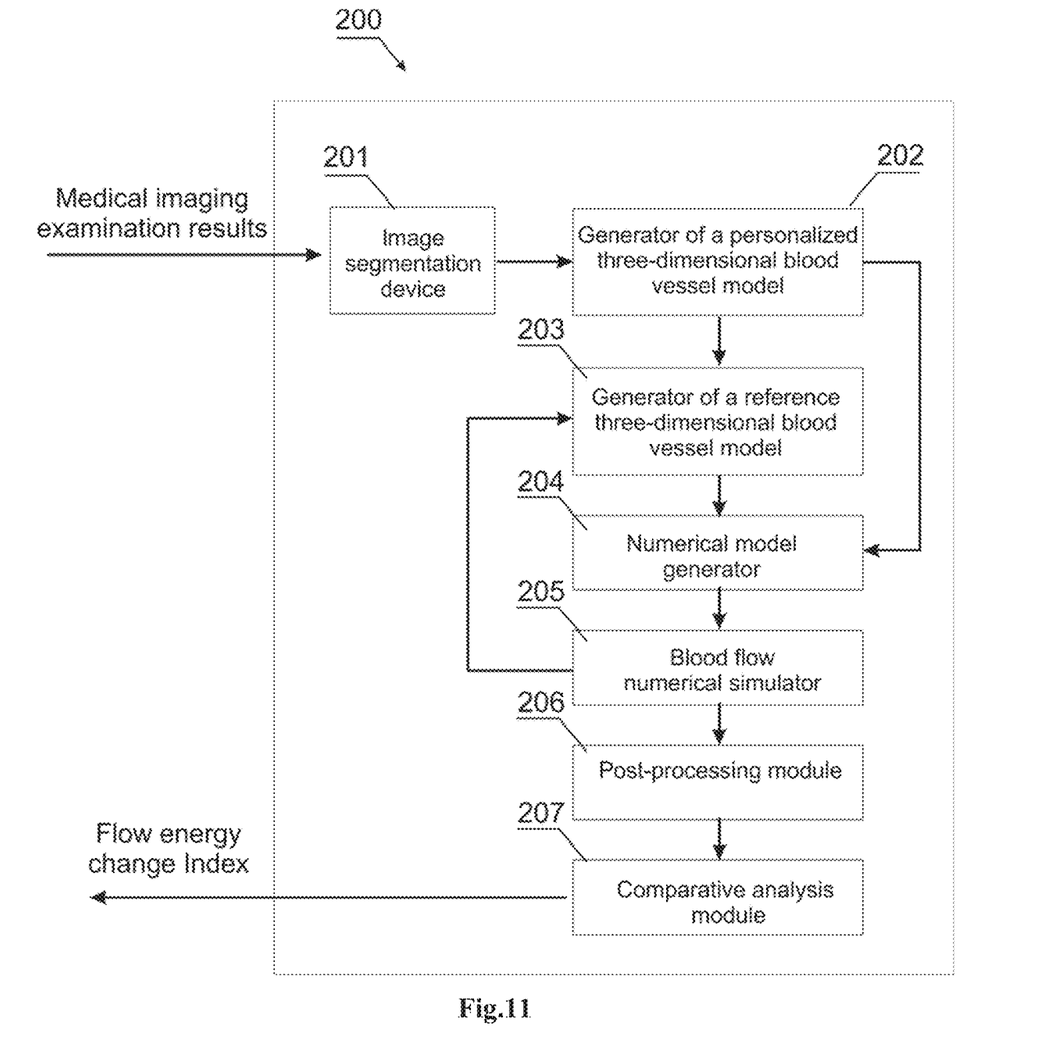
FIG. 11 shows an example of a system for conducting the method according to an embodiment of the invention.

FIG. 11 shows an example of a system for conducting the method according to the invention. The system 200 comprises a first generator 202 for generating the three-dimensional personalized model 1 of blood vessels and a second generator 203 for generating the three-dimensional reference model 6 of blood vessels. The personalized model 1 is generated based on medical imaging data which are received and processed by an image segmentation device 201. Wherein the reference three-dimensional model is generated based on the medical imaging data or based on the personalized three-dimensional model generated by the generator 202. The system 200 further comprises a numerical model generator 204 for preparing numerical models for the personalized model and for the reference model with predetermined identical boundary conditions and initial conditions. The blood flow in the numerical models is simulated by a blood flow numerical simulator 205 which provides (accordingly to the established boundary and initial condition) parameters of the blow flow such as flow rate, local pressure and velocity values, flow energy values for all branches of both models. The obtained data is analyzed by a post-processing module 206 and the obtained values are compared in a comparative analysis module 207 in which among others, the flow energy change indexes (absolute and relative) are determined (ΔEf, EFR).

All components of the system 200 can be controlled by one or more computers which is controlled by an operating system and one or more software applications. The computer may be equipped with a suitable memory which may store computer program or programs executed by the computer in order to execute steps of the methods utilized in the system. Computer programs are preferably stored on a non-transitory medium. An example of a non-transitory medium is a non-volatile memory, for example a flash memory while an example of a volatile memory is RAM. The computer instructions are executed by a processor. These memories are exemplary recording media for storing computer programs comprising computer-executable instructions performing all the steps of the computer-implemented method according the technical concept presented herein. Communication between the computers and the components of the system may be performed by wire or wirelessly, according to known communication means.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A method for modelling blood vessels, the method comprising:
   obtaining medical imaging data of the blood vessels;
   generating a three-dimensional personalized model of the blood vessels, based on the medical imaging data;
   generating a three-dimensional reference model of the blood vessels that reflects a state of healthy blood vessels that lack lesions, based on the medical imaging data or based on numerical reconstruction of the personalized model;
   performing a numerical simulation of blood flow for the same physical and boundary conditions in the personalized model and in the reference model, the simulation comprising determining conditions of blood flow at an inlet to the personalized model and calculating blood flow energy for the inlet to the personalized model and all outlets of the personalized model and determining conditions of blood flow at an inlet to the reference model and calculating blood flow energy for the inlet to the reference model and all outlets of the reference model;
   comparing the blood flow energy $E_f$ measured for the personalized model and for the reference model wherein the blood flow energy $E_f$ is defined as a product of a total pressure and a mass flow rate calculated according to equation:

$$Ef = \left(\frac{1}{2}U^2 + \frac{P}{\rho}\right)Q = P_{total}Q$$

wherein ½ U² is a dynamic pressure, P/ρ is a static pressure, $P_{total}$ is the total pressure and Q is the flow rate through a surface perpendicular to an axis of the blood vessel; and determining flow energy change indexes ΔEf of the blood flow in branches based on the blood flow energy in the personalized model and in the reference model, wherein the energy change index ΔEf is calculated according to equation:

$$\Delta Ef = Ef_{sten} - Ef_0$$

wherein $Ef_{sten}$ is the flow energy in the branch of the personalized model and $Ef_0$ is the flow energy in the same branch of the reference model.

2. The method according to claim 1, comprising generating the reference model based on the personalized model, by eliminating stenoses existing in the personalized model, resulting from atherosclerosis lesions, by numerical modification of the blood vessel geometry in areas of said stenoses to obtain a hypothetically healthy blood vessel model, as the reference model prior to the onset of the lesions.

3. The method according to claim 1, comprising generating the reference model based on the personalized model, by eliminating one stenosis, in one branch only, without reconstruction changes in geometry in other branches.

4. The method according to claim 1, comprising conducting the blood flow simulation for both personalized and reconstructed models, for an increasing inlet blood flow rate, from laminar flow until achieving a developed turbulent flow.

5. The method according to claim 1, comprising applying a variable blood flow rate on the inlet of both personalized and reconstructed models.

6. The method according to claim 1, comprising conducting the blood flow simulation in the personalized model for inlet and outlet boundary conditions obtained from the simulation results of the reference model.

7. The method according to claim 5, comprising simulating a linear increase of blood flow rate on the inlet to the personalized model and on the inlet to the reference model.

8. The method according to claim 5, comprising simulating a pulsatory change of blood flow rate, having a variable amplitude or a variable frequency, on the inlet to the personalized model and on the inlet to the reference model.

9. The method according to claim 1, further comprising determining an absolute flow energy change index, as a difference between the flow energy in the branch of the personalized model and the flow energy in the same branch of the reference model.

10. The method according to claim 1, further comprising determining a relative flow energy change index, as a relationship of the flow energy in any selected, one or more, branches of the models, for both the personalized model and the reference model, in relation to the inlet energy of flow.

11. The method according to claim 1, comprising determining the flow energy change indexes on a basis of linear or polynomial approximations of a function of the flow energy change with respect to the flow rate (EFR).

12. The method according to claim 1, comprising determining the indexes of flow energy change during the diastolic phase in wave free period, when the hemodynamic conditions are substantially independent on the pulse rate, as well when the resistance is minimal, substantially constant and a pressure gradient is proportional to the flow rate.

13. The method according to claim 1, comprising determining other, absolute and relative indexes of hemodynamics parameters, including at least one of:

vascular resistance, pressure drop (dP), turbulence kinetic energy, wall shear stress, oscillatory shear and residence time, which are a function of pressure (stress) and flow rate of the personalized model compared to the reference model.

14. A computer-implemented system for modelling blood vessels, the system comprising:

an input for obtaining medical imaging data of the blood vessels;

a personalized model generator configured to generate a three-dimensional personalized model of the blood vessels, based on the medical imaging data;

a reference model generator configured to generate a three-dimensional reference model of the blood vessels that reflects a state of healthy blood vessels that lack lesions, based on the medical imaging data or based on numerical reconstruction of the personalized model;

a blood flow numerical simulator configured to perform a numerical simulation of blood flow for the same physical and boundary conditions in the personalized model and in the reference model, the simulation comprising determining conditions of blood flow at an inlet to the personalized model and calculating blood flow energy for the inlet and all outlets of the personalized model and determining conditions of blood flow at an inlet to the reference model and calculating blood flow energy for the inlet and all outlets of the reference model; and a comparative analysis module configured to:

compare the blood flow energy $E_f$ measured for the personalized model and for the reference model wherein the blood flow energy $E_f$ is defined as a product of a total pressure and a mass flow rate calculated according to equation:

$$Ef = \left(\frac{1}{2}U^2 + \frac{P}{\rho}\right)Q = P_{total}Q$$

wherein ½ U² is a dynamic pressure, P/ρ is a static pressure, $P_{total}$ is the total pressure and Q is the flow rate through a surface perpendicular to an axis of the blood vessel and determine flow energy change indexes ΔEf of the blood flow in branches based on the blood flow energy in the personalized model and in the reference model wherein the energy change index ΔEf is calculated according to equation:

$$\Delta Ef = Ef_{sten} - Ef_0$$

wherein $Ef_{sten}$ is the flow energy in the branch of the personalized model and $Ef_0$ is the flow energy in the same branch of the reference model.

* * * * *